(12) United States Patent
Okamura

(10) Patent No.: US 10,194,807 B2
(45) Date of Patent: Feb. 5, 2019

(54) BODY SURFACE THERMOMETER AND WEARABLE TEMPERATURE MEASURING DEVICE

(71) Applicant: BOE TECHNOLOGY GROUP CO., LTD., Beijing (CN)

(72) Inventor: Masakazu Okamura, Beijing (CN)

(73) Assignee: BOE TECHNOLOGY GROUP CO., LTD., Beijing (CN)

( * ) Notice: Subject to any disclaimer, the term of this patent is extended or adjusted under 35 U.S.C. 154(b) by 421 days.

(21) Appl. No.: 14/443,807

(22) PCT Filed: Sep. 30, 2014

(86) PCT No.: PCT/CN2014/087901
§ 371 (c)(1),
(2) Date: May 19, 2015

(87) PCT Pub. No.: WO2015/192539
PCT Pub. Date: Dec. 23, 2015

(65) Prior Publication Data
US 2016/0256055 A1  Sep. 8, 2016

(30) Foreign Application Priority Data
Jun. 20, 2014 (CN) .......................... 2014 1 0281370

(51) Int. Cl.
*A61B 5/01* (2006.01)
*A61B 5/00* (2006.01)
(Continued)

(52) U.S. Cl.
CPC .............. *A61B 5/01* (2013.01); *A61B 5/0075* (2013.01); *A61B 5/6831* (2013.01);
(Continued)

(58) Field of Classification Search
None
See application file for complete search history.

(56) References Cited

U.S. PATENT DOCUMENTS 4,797,840 A * 1/1989 Fraden .................. G01J 5/0022
                                                    374/133
5,316,854 A * 5/1994 Lin ........................ C03C 17/007
                                                   106/287.13
(Continued)

FOREIGN PATENT DOCUMENTS

CN           1113319 A      12/1995
CN         101999887 A       4/2011
(Continued)

OTHER PUBLICATIONS

Third Chinese Office Action dated Jul. 25, 2016; Appln. No. 201410281370.7.
(Continued)

*Primary Examiner* — Michael Carey
*Assistant Examiner* — Farouk Bruce
(74) *Attorney, Agent, or Firm* — Ladas & Parry LLP

(57) ABSTRACT

A body surface thermometer and a wearable temperature measuring device are disclosed. The body surface thermometer includes an infrared temperature sensor and a shielding protective hood disposed outside the infrared temperature sensor, and the shielding protective hood is an infrared ray shielding protective hood. With the body surface thermometer, the measuring precision of surface temperature of a target object can be promoted, thereby raising the freedom degree of test.

6 Claims, 3 Drawing Sheets

(51) Int. Cl.
  *G01J 5/04* (2006.01)
  *G01J 5/00* (2006.01)
  *G02B 5/20* (2006.01)
  *G01K 13/00* (2006.01)
  *G01J 5/06* (2006.01)

(52) U.S. Cl.
  CPC ............ *G01J 5/0025* (2013.01); *G01J 5/048* (2013.01); *A61B 5/6824* (2013.01); *A61B 5/742* (2013.01); *A61B 2562/0271* (2013.01); *A61B 2562/185* (2013.01); *G01J 2005/065* (2013.01); *G01K 13/004* (2013.01); *G02B 5/208* (2013.01)

(56) References Cited

U.S. PATENT DOCUMENTS

| | | | |
|---|---|---|---|
| 5,645,349 | A | 7/1997 | Fraden |
| 5,672,931 | A * | 9/1997 | Kiss ............. F21V 13/08 313/24 |
| 5,693,942 | A * | 12/1997 | Endo ............. G01J 5/20 250/338.1 |
| 5,860,740 | A * | 1/1999 | Fujima ........... G01J 5/02 368/11 |
| 5,893,643 | A * | 4/1999 | Kumar ......... H01L 21/67248 118/712 |
| 6,585,684 | B1 * | 7/2003 | Hughett ......... A61N 5/1007 604/131 |
| 6,846,106 | B1 | 1/2005 | Chen et al. |
| 2007/0118045 | A1 | 5/2007 | Naghavi et al. |
| 2007/0293792 | A1 * | 12/2007 | Sliwa ............. A61B 5/11 600/587 |
| 2011/0030728 | A1 * | 2/2011 | Semmer .......... B08B 3/02 134/18 |
| 2011/0228811 | A1 * | 9/2011 | Fraden ........... G01J 5/061 374/130 |
| 2012/0101350 | A1 | 4/2012 | Bychkov |
| 2012/0316459 | A1 | 12/2012 | Abreu |
| 2013/0308676 | A1 | 11/2013 | Ha |
| 2014/0018686 | A1 | 1/2014 | Medelius et al. |

FOREIGN PATENT DOCUMENTS

| | | |
|---|---|---|
| CN | 102141442 A | 8/2011 |
| CN | 102940494 A | 2/2013 |
| CN | 103054560 A | 4/2013 |
| CN | 104000571 A | 8/2014 |
| CN | 104055502 A | 9/2014 |
| EP | 1061348 A2 | 12/2000 |
| JP | 0454935 A | 2/1992 |
| JP | 2012-098041 A | 5/2012 |
| WO | 2011057089 A1 | 5/2011 |

OTHER PUBLICATIONS

International Search Report & Written Opinion Appln. No. PCT/CN2014/087901; dated Mar. 27, 2015.

First Chinese Office Action Appln. No. 201410281370.7; dated Aug. 25, 2015.

Second Chinese Office Action Appln. No. 201410281370.7; dated Mar. 10, 2016.

Extended European Search Report dated Feb. 26, 2018; Appln. No. 14859313.0.

* cited by examiner

BODY SURFACE THERMOMETER AND WEARABLE TEMPERATURE MEASURING DEVICE

TECHNICAL FIELD

Embodiments of the present invention relate to a body surface thermometer and a wearable temperature measuring device.

BACKGROUND

In the field of health and medicine, body temperature or body surface temperature is a piece of important information for human signs.

In the past, people designed and used various kinds of thermometers. However, in order that the influence of ambient temperature can be avoided so as to measure the temperature more accurately, it usually takes a very long time to conduct measurements. As temperature measuring methods, there are contact type and non-contact type. For a contact type, the body temperature is measured by allowing a temperature sensor unit of a thermometer and the body surface temperature to reach an equilibrium state. In such a case, in order not to receive the image of surroundings, the measurement will be generally made in a mouth, or under an armpit. For non-contact type, infrared rays radiated from the body surface are detected and converted into the body temperature. In such a case, in order to avoid the influence of the surrounding infrared rays, the measurement will usually be made in an ear.

Along with the continued research, for the sake of clearly understanding the state of a body, people begin to consider measuring the body surface temperature at the wrist or the like, and put forward a wrist type thermometer. When the wrist type thermometer is compared with common thermometers used in a mouth, under an armpit and in an ear, there are many situations of incomplete contact with the body surface in its actual use. Furthermore, because it is worn at the wrist and is easily affected by the surroundings, the measuring precision is not high.

SUMMARY

According to embodiments of the present invention, there is provided a body surface thermometer, which includes an infrared temperature sensor and a shielding protective hood disposed outside the infrared temperature sensor, and the shielding protective hood is an infrared ray shielding protective hood.

For example, the shielding protective hood has an opening on one side acting to cover over a body surface whose temperature is to be measured, and the infrared temperature sensor is located on an inner wall of the shielding protective hood that directly faces the opening.

For example, the shielding protective hood is made of quartz glass.

For example, an outer surface of the shielding protective hood is coated with an ultraviolet ray transmission proofing layer.

For example, an outer surface of the shielding protective hood is coated with a visible light transmission proofing layer.

For example, the body surface thermometer further includes a measurement display unit, connected to the infrared temperature sensor, which acts to display measured results of the body surface temperature.

According to an embodiment of the invention, there is further provided a wearable temperature measuring device, which includes a wearing body and a body surface thermometer disposed on the wearing body, the body surface thermometer being the body surface thermometer as any of above-mentioned items, with the measurement display unit connected to the infrared temperature sensor being mounted on the wearing body.

For example, the wearing body is a flexible circular ring.

BRIEF DESCRIPTION OF THE DRAWINGS

In order to illustrate the technical solution of the embodiments of the invention more clearly, the drawings of the embodiments will be briefly described below; it is obvious that the drawings as described below are only related to some embodiments of the invention, but not limitative of the invention.

DETAILED DESCRIPTION

In order to make objects, technical details and advantages of the embodiments of the invention apparent, hereinafter, the technical solutions of the embodiments of the invention will be described in a clearly and fully understandable way in connection with the drawings related to the embodiments of the invention. It is obvious that the described embodiments are just a part but not all of the embodiments of the invention. Based on the described embodiments of the invention, those ordinarily skilled in the art can obtain other embodiment(s), without any inventive work, which should be within the scope sought for protection by the invention.

According to the relationship between an absolute temperature T and the wavelength λ of radiated infrared rays:

$$\lambda(\mu m) = 2897/T$$

If the body temperature is 35□, the wavelength of radiated infrared rays is about 9.4 μm; when the body temperature is 4□, the wavelength of radiated infrared rays is about 9.2 μm; and when the normal temperature value of the human body's surface is between 36□ and 37□, infrared rays at 9.5 μm or so will be radiated.

Figure 1:
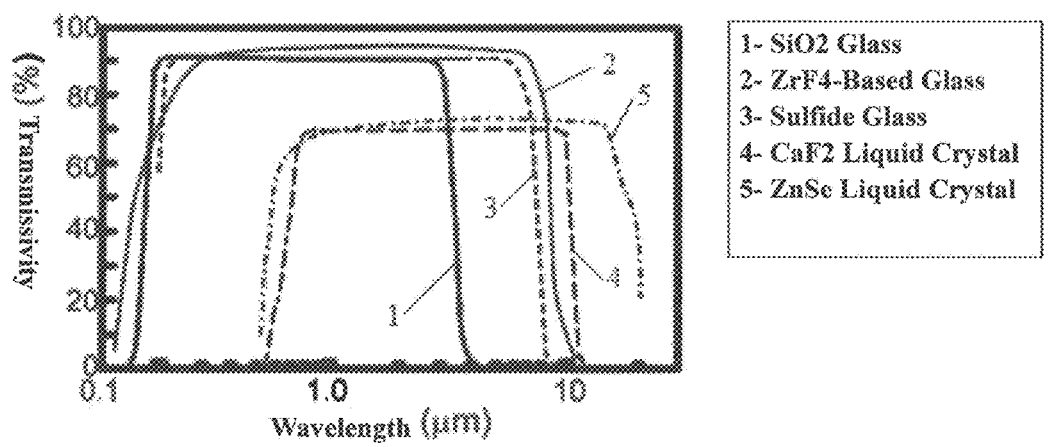
FIG. 1 is a schematic diagram illustrating the transmissivity-wavelength characteristics of different materials with regard to glass.

Referring to that shown in FIG. 1, for common quartz glass, light in the ultraviolet domain or visible light domain are easy to be transmitted through it, and with respect to far infrared rays above 5 μm, it has such a light transmission characteristics that rays are not easy to be transmitted through it.

Figure 2:
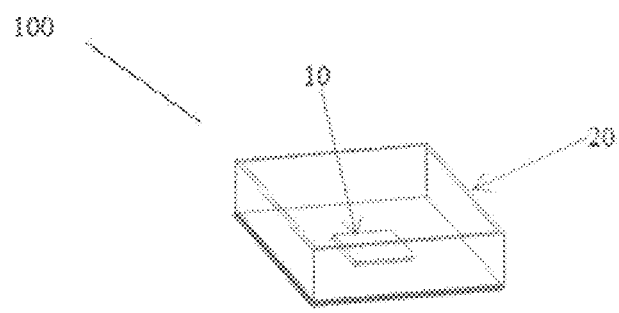
FIG. 2 is a structurally schematic view illustrating a body surface thermometer according to an embodiment of the invention.

Referring to that shown in FIG. 2, a body surface thermometer according to an embodiment includes an infrared temperature sensor 10 and a shielding protective hood 20 disposed outside the infrared temperature sensor 10, and the shielding protective hood is an infrared-ray shielding protective hood. For example, the shielding protective hood 20 surrounds the infrared temperature sensor 10, but a measuring opening is set aside. For example, the shielding protective hood 20 is arranged to be a tank-shaped structure that is opened on one side, and the infrared temperature sensor 10 is disposed on an inner wall of the shielding protective hood 20. When it is used for measurement of body surface temperature, the opening is made to cover a body surface, and the infrared temperature sensor does not contact with the body surface, so as to make a non-contact type measurement.

For example, in order to enhance the precision of the temperature measurement, the infrared temperature sensor 10 is preferably disposed on an inner wall of the shielding protective hood 20 that directly faces the opening. Thus, it is can be realized that, upon measurement of the body surface temperature, the opening covers over a body surface, and the infrared temperature sensor 10 directly faces the measured body surface. The infrared temperature sensor 10 can fully receive infrared rays emitted from the measured site, thereby enhancing the precision of temperature measurement.

In the above-described body surface thermometer, because non-contact type measurement is performed, the freedom degree of measurement is higher, and to make a temperature measurement by utilizing infrared rays radiated by a body surface saves more time than that for a commonly used measuring mode of being performed in a mouth, under an armpit or in an ear. The shielding protective hood 20 can act to prevent the leakage of infrared rays emitted from the body surface, so that external infrared rays are prevented from affecting the measurement for body surface temperature, and also can act to block the effects of ambient air convection on the body surface temperature, so that the precision of measurement is enhanced.

For example, on the grounds that the shielding characteristic of quartz glass against infrared rays is somewhat more superior, quartz glass can be selected for producing the shielding protective hood according to the embodiment. The shielding protective hood may be of any shape (e.g., circular, square, or the like), as long as the influence of surroundings can be reduced and the site to be measured can be shielded favorably.

For example, in order to avoid the interference from ultraviolet rays in the neighborhood of a test environment, an UV light transmission proofing layer may be further coated on an outer surface of the shielding protective hood according to the embodiment; and in order to avoid the interference from visible light in the neighborhood of the test environment, a visible light transmission proofing layer may be coated on an outer surface of the shielding protective hood.

Figure 4:
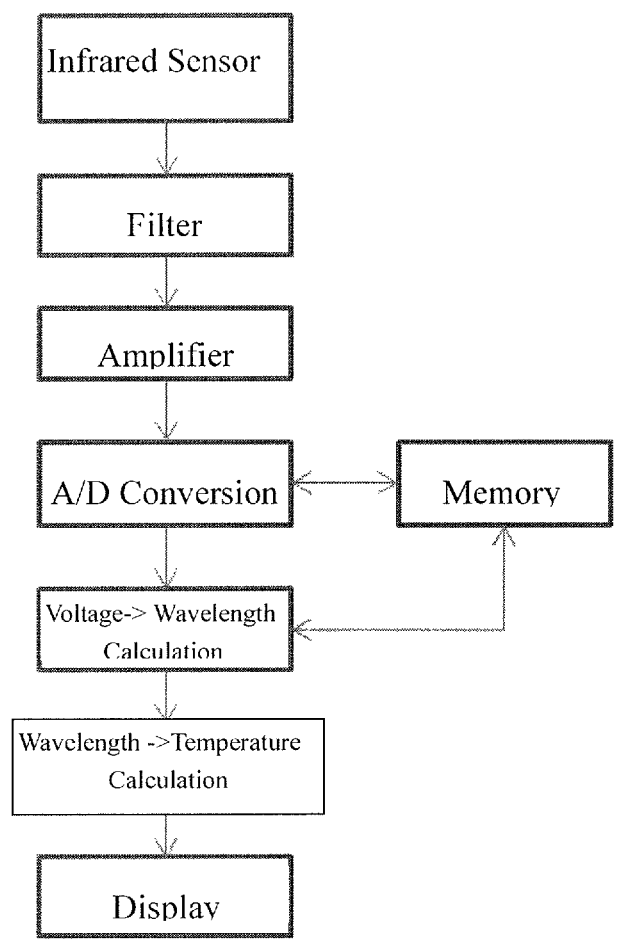
FIG. 4 is a flowchart illustrating the temperature measurement of a body surface thermometer according to an embodiment of the invention.

The body surface thermometer according to the embodiment may further include a measurement display unit connected to the infrared temperature sensor, and the measuring results of body surface temperature are displayed by the measurement display unit. For example, referring to that shown in FIG. 4, after the infrared rays emitted from a body surface at a measured site are received by the infrared temperature sensor, they are filtered by a filter, amplified by an amplifier, and supplied to an A/D converter for data conversion sequentially. With the use of the information for comparison stored in a memory, the wavelength value is calculated by the voltage, then the temperature is calculated by the wavelength value, and finally, display of the temperature is conducted by the measurement display unit.

Figure 3:
FIG. 3 is a schematic view illustrating application of a body surface thermometer to the measurement of the body surface temperature according to an embodiment of the invention.
Figure 3:
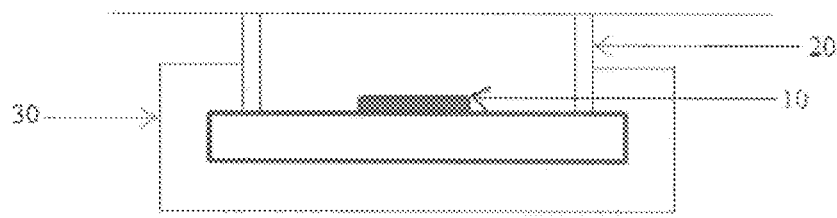

Based on the above body surface thermometer, according to an embodiment of the invention, there is further provided a wearable temperature measuring device. As shown in FIG. 3, the wearable display device includes a wearing body 30 and a body surface thermometer (as represented by an infrared temperature sensor 10 and a shielding protective hood 20 in FIG. 3) disposed on the wearing body 30, and a measurement display unit is mounted on the wearing body. The wearing body 30 is made to be a flexible circular ring, so as to form a wrist type body surface thermometer. While the wearable temperature measuring device is used for measurement of body surface temperature, the wearing body 30 is fixed at a body-surface measuring site 40, so that the infrared temperature sensor 10 is located directly above the body-surface measuring site 40, a temperature measuring function is started, and further, the measured temperature is displayed by the measurement display unit mounted on the wearing body 30.

Figure 5:
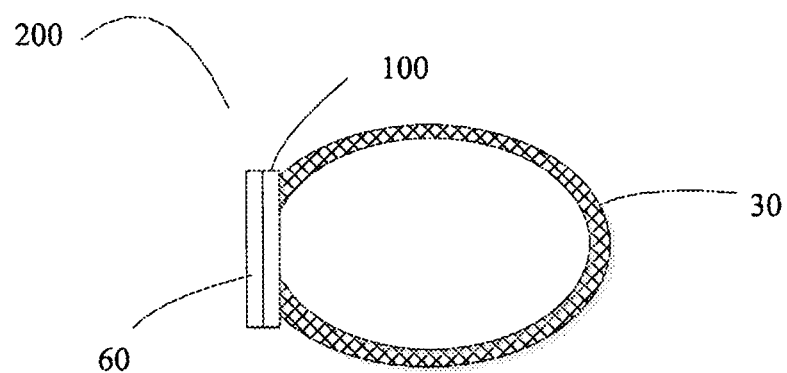
FIG. 5 is a schematic view illustrating a structure of a wearable temperature measuring device according to an embodiment of the invention.

FIG. 5 illustrates a structure of a wearable temperature measuring device 200 and the connection relationship of elements of the wearable temperature measuring device 200. As illustrated, the wearable temperature measuring device 200 comprises a wearing body 30 and a body surface thermometer 100 disposed on the wearing body 30. A measurement display unit 60 is mounted on a wearing body 30, and is connected to an infrared temperature sensor 10 in the body surface thermometer 100.

As can be seen from the above, according to at least an embodiment of the invention, with the aid of an infrared-ray shielding function possessed by the shielding protective hood, surrounding far infrared rays are blocked, and moreover, the effect of ambient air convection on the measurement of the infrared temperature sensor is blocked. Thus, the influence of far infrared rays in the surrounding environment on the temperature measurement is reduced, and the measuring precision of surface temperature of a target object is promoted. The infrared temperature sensor is involved in a non-contact type measurement relative to a surface of the target object, so as to raise the freedom degree of test.

Descriptions made above are merely exemplary embodiments of the present invention, but are not used to limit the protection scope of the invention. The protection scope of the invention is determined by the attached claims.

This application claims the benefit of priority from Chinese patent application No. 201410281370.7, filed on Jun. 20, 2014, the disclosure of which is incorporated herein in its entirety by reference as a part of the present application.

What is claimed is:

1. A body surface thermometer, comprising an infrared temperature sensor and a shielding protective hood disposed outside the infrared temperature sensor and enclosing the infrared temperature sensor, the shielding protective hood being an infrared ray shielding protective hood;
    wherein the shielding protective hood is made of quartz glass and an outer surface of the shielding protective hood is coated with an ultraviolet ray transmission proofing layer.

2. The body surface thermometer claimed as claim 1, wherein the shielding protective hood has an opening on one side, the infrared temperature sensor is located on an inner wall of the shielding protective hood, and the opening is disposed directly over the infrared temperature sensor.

3. The body surface thermometer claimed as claim 2, further comprising a measurement display unit, connected to the infrared temperature sensor, which acts to display measured results of the body surface temperature.

4. The body surface thermometer claimed as claim 3, wherein an outer surface of the shielding protective hood is further coated with a visible light transmission proofing layer.

5. The body surface thermometer claimed as claim 1, further comprising a measurement display unit, connected to the infrared temperature sensor, which acts to display measured results of the body surface temperature.

6. The body surface thermometer claimed as claim 1, wherein an outer surface of the shielding protective hood is coated with a visible light transmission proofing layer.

* * * * *